United States Patent [19]

Albal et al.

[11] Patent Number: 5,731,446
[45] Date of Patent: Mar. 24, 1998

[54] MOLYBDENUM EPOXIDATION CATALYST RECOVERY

[75] Inventors: Rajendra S. Albal, West Chester; Thomas I. Evans, Glenmoore; W. Wayne Wentzheimer, Glen Mills; Allen M. Donn, Parkside; Morris Gelb, Bryn Mawr, all of Pa.

[73] Assignee: ARCO Chemical Technology, L.P., Greenville, Del.

[21] Appl. No.: 658,677

[22] Filed: Jun. 4, 1996

[51] Int. Cl.⁶ .................................................. C07D 301/19
[52] U.S. Cl. .......................... 549/529; 210/688; 423/54
[58] Field of Search ........................ 549/529; 210/688; 423/54

[56] References Cited

U.S. PATENT DOCUMENTS

| | | |
|---|---|---|
| 3,351,635 | 11/1967 | Kollar . |
| 3,463,604 | 8/1969 | Tave ........................... 549/529 |
| 4,189,381 | 2/1980 | Caferty et al. ............... 210/688 |
| 4,239,865 | 12/1980 | Tarao et al. ................. 210/688 |
| 4,405,572 | 9/1983 | Moore et al. . |
| 5,093,509 | 3/1992 | Meyer et al. ................. 549/529 |
| 5,101,052 | 3/1992 | Meyer et al. ................. 549/529 |
| 5,171,868 | 12/1992 | Albal et al. . |
| 5,210,354 | 5/1993 | Dubner et al. . |
| 5,276,235 | 1/1994 | Dubner . |
| 5,439,657 | 8/1995 | Wong et al. . |
| 5,585,077 | 12/1996 | Evans et al. ................. 423/58 |

FOREIGN PATENT DOCUMENTS

| | | | |
|---|---|---|---|
| 3901006 | 7/1990 | Germany ..................... | 210/688 |
| 28354 | 3/1976 | Japan ......................... | 210/688 |

*Primary Examiner*—Wayne Langel
*Attorney, Agent, or Firm*—Stephen D. Harper; William C. Long

[57] ABSTRACT

An aqueous epoxidation process stream containing molybdenum and sodium values and organics is treated for organics removal as by incineration and an aqueous solution containing molybdenum and sodium is recovered, cooled, acidified and contacted with activated carbon and an aqueous stream reduced in molybdenum is recovered, further molybdenum reduction can be achieved by treatment with basic ion exchange resin.

7 Claims, 1 Drawing Sheet

MOLYBDENUM EPOXIDATION CATALYST RECOVERY

BACKGROUND OF THE INVENTION

1. Field of the Invention

The production of oxirane compounds such as propylene oxide by the catalytic reaction of an olefin with an organic hydroperoxide is a process of great commercial importance. Generally a homogeneous molybdenum catalyst is employed. The Oxirane Process for the co-production of propylene oxide and styrene monomer is illustrative of this technology.

The process of this invention relates to the recovery of molybdenum epoxidation catalyst values from process streams in such epoxidation process technology.

2. Description of Related Act

An extremely successful process for the co-production of propylene oxide and styrene monomer involves the molecular oxygen oxidation of ethyl benzene to form ethyl benzene hydroperoxide, the catalytic reaction of the hydroperoxide with propylene to form propylene oxide and 1-phenyl ethanol, and the dehydration of the 1-phenyl ethanol to styrene monomer. The basic patent describing this process is U.S. Pat. No. 3,351,635.

In practice of the process, the epoxidation reaction mixture, usually after separation of unreacted propylene by distillation, is treated with aqueous caustic in an amount in excess of that necessary both to react with contained molybdenum values to form sodium molybdate and to react with organic impurities such as acids and phenols which are also contained in the epoxidate. See U.S. Pat. Nos. 4,405,572, 5,210,354, 5,276,235, and 5,171,868, for example.

A problem which has existed in such prior practices has been the formation of relatively large quantities of an aqueous process stream containing molybdenum, sodium and organics, and the disposal of such aqueous process streams. The presence of molybdenum is particularly troublesome since this material must be removed prior to outfall to satisfy environmental restrictions.

U.S. Pat. No. 5,439,657 and commonly assigned application Ser. No. 08/510,727 filed Aug. 3, 1995, U.S. Pat. No. 5,585,077, are concerned with such molybdenum containing streams and separation of molybdenum therefrom.

Despite the substantial prior work, there still remains room for improvement in the treatment of the process streams, and especially in molybdenum removal, in light of increasingly stringent environmental considerations.

BRIEF DESCRIPTION OF THE INVENTION

The aqueous epoxidation process stream containing molybdenum and sodium values as well as organics is treated by known methods, as by incineration, to first separate organics prior to the carbon bed treatment. During the incineration process, particulate ash comprised of the molybdenum and sodium values, passes downwardly through the incinerator with the incinerator gases. The ash-containing gases are quenched by admixing with water to form the incinerator blowdown stream. The blowdown is an aqueous solution of the molybdenum value, as sodium molybdate, and sodium value, as sodium carbonates, from the epoxidation process stream. The blowdown solution may not be directly discharged due to environmental hazards associated with the molybdenum heavy metal contained therein. In accordance with the present invention, the substantially organics free aqueous blowdown stream, preferably after being cooled, is acidified, as with $H_2SO_4$, so that carbonates are converted to $CO_2$ which can readily be removed. Thereafter, the essentially carbonate-free stream is contacted with solid activated carbon adsorbent to separate molybdenum values contained therein. The resulting aqueous solution greatly reduced in contained molybdenum can then be conveniently disposed of or, if maximum molybdenum specifications are very stringent, the aqueous effluent from the carbon treatment is further treated by contact with a basic ion exchange thereby to effectuate substantially complete molybdenum removal.

In place of incineration, other known procedures such as wet air oxidation or biotreatment may be used to remove organic materials prior to carbon treatment. In such cases, acidification as above described to separate $CO_2$ is not necessary. Incineration does, however, represent the preferred method for separating the organic materials.

DESCRIPTION OF THE DRAWING

The attached drawing illustrates in schematic form practice of the invention.

DETAILED DESCRIPTION

Figure 1:
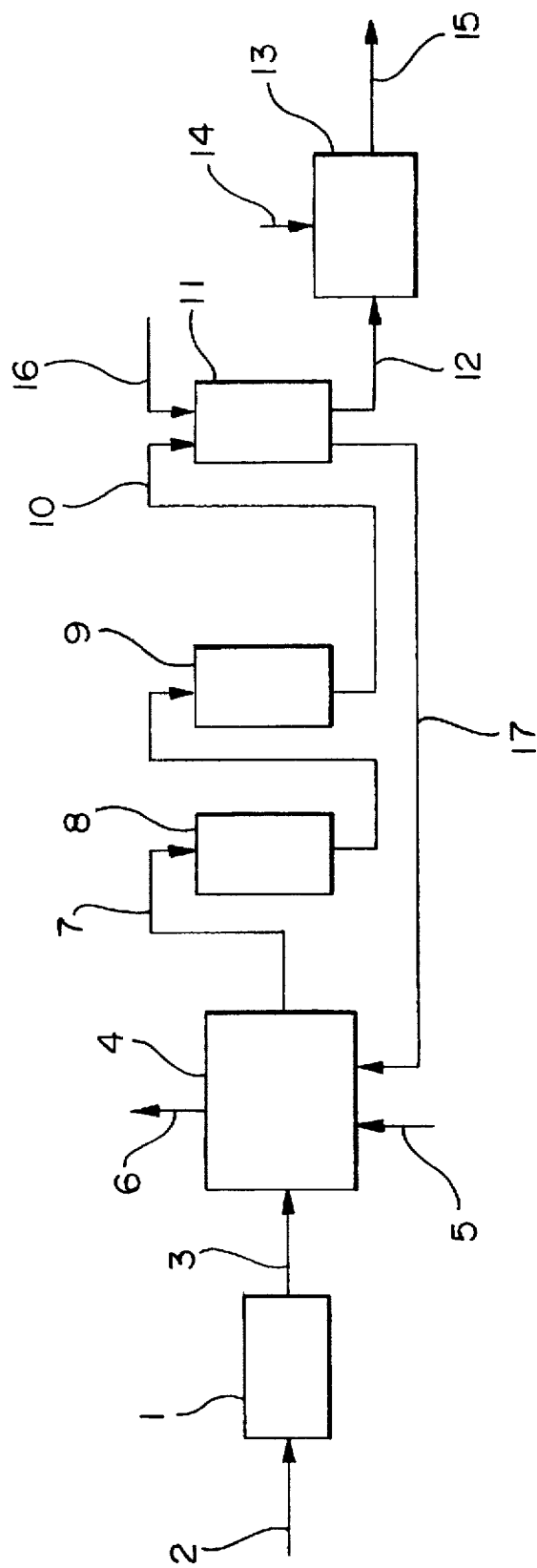

In accordance with preferred practice of the present invention, an aqueous epoxidation stream containing molybdenum catalyst values, sodium values from caustic treatment and organic materials is incinerated in accordance with known procedures. Essentially complete combustion of organics is achieved. The molybdenum and sodium values, primarily as sodium molybdate and sodium carbonate, are recovered as an aqueous incinerator blowdown stream.

The molybdenum and sodium containing blowdown stream is cooled and then acidified to a pH of 5 or lower as by addition of sulfuric acid or HCl, and with appropriate agitation the carbonates are converted to $CO_2$ which is vaporized and separated. The sodium is converted to the sodium salt of the added acid. Temperatures of 10° C. to 50° C. can be employed to accomplish $CO_2$ removal while minimizing corrosion and special materials of construction.

The acidified blowdown solution after $CO_2$ removal, or the equivalent acidic aqueous molybdenum containing stream where other organics removal procedures are used, is then contacted with solid activated carbon whereby the great predominance of the molybdenum values in the aqueous stream are adsorbed on the carbon and thus effectively removed from the aqueous stream. One or more carbon beds are employed which can be disposed of or regenerated by aqueous caustic wash when the molybdenum removal capacity has declined to a certain level.

The above procedure is effective in reducing the level of contained molybdenum in the aqueous process stream from more than 1000 ppm by weight to about 50 ppm or less.

Where lower levels of molybdenum in plant outflow streams are required, in especially preferred practice the aqueous stream after carbon treatment is further contacted with a basic or chelating ion exchange resin to achieve essentially complete molybdenum separation—ie, to produce an aqueous stream having less than about 10 ppm molybdenum.

Useful activated carbons or charcoals include those obtained from lignite, gas black, coconut, bagasse, wood, sawdust, peat, pulp-mill waste, blood, bone, etc. Specific activated carbons include Calgon Corporation granular carbons such as Calgon F-400, F-200 or react AW, NORIT granular activated carbons such as NORIT C, Cenco activated carbons, products of Central Scientific Company, Nuchar activated carbons, products of West Virginia Pulp and Paper Company, and products of Darco Division, ICI AMERICAS, Inc. Rohm and Haas Ambersorb carbonaceous adsorbents such as X-340 and the like can be employed as can Rohm and Haas activated Amberlite. Illustrative commercially available carbons include Type CAL granular carbon (Calgon Corporation) and NORIT ROW 0.8 granular activated carbon (NORIT Corporation).

Ion exchange resins which can be employed in practice of the invention are basic anion exchange resins which are well known articles of commerce. Both strong-base resins and weak-base resins can be used.

Strong-base resins can be produced by the reaction between chlormethylated styrene-DVB copolymer and a tertiary amine such as trimethyl amine, which results in a resin with quaternary ammonium groups.

The principal types of weak-base anion exchanges are amine derivatives of styrene-DVB copolymers, epichlorohydrin-amine condensation products, and amine derivatives of phenol-formaldehyde products, and may contain primary, secondary or tertiary amine groups, or mixtures of some or all of these groups.

Weak-base styrene-DVB resins can be made. For example, by aminating chloromethylated copolymer in much the same way that strong-base styrene-DVB resins are made except that primary or secondary amines are generally used instead of a tertiary amine.

U.S. Pat. Nos. which describe the preparation of basic anion resins useful in the present invention include: 4,025,467, 3,791,996, 3,817,878, 3,346,516, 4,082,701, 3,843,566, 3,813,353, 3,812,061, 3,882,053, 3,793,273, 3,296,233, 3,108,922, 3,005,786, 3,637,535 and 4,052,343.

For a further description of the invention, reference is made to the accompanying drawing, FIG. 1. Referring to FIG. 1, aqueous incinerator blowdown is introduced into cooling zone 1 via line 2. In zone 1 the temperature of the aqueous stream is reduced from about 90° C. by conventional heat exchange procedures to 40° C. or less. The cooled stream passes via line 3 to zone 4 where it is acidified from a pH of about 9.5 to a low ie. 5 or less, preferably 1-3, by addition of sulfuric acid via line 5. Other acids such as hydrochloric acid can be used.

By this acidification, carbonate values in the aqueous stream are converted to carbon dioxide which is normally gaseous and which is removed as vapor via line 6. A stripping gas such as nitrogen (not shown) can be introduced into zone 4 to aid in CO₂ removal.

The substantially carbonate-free solution is passed via line 7 from zone 4 to contact with beds of solid activated carbon in zones 8 and 9. Although the carbon contact is shown as taking place in two zones, it will be understood that a greater or lesser number of contact zones can conveniently be employed.

As a result of the above described treatment, the contained molybdenum content can be reduced from 1000 ppm to 50 ppm or less in the stream leaving the carbon treatment zone 9.

It should be noted that the acidification prior to carbon bed contact is essential. Where the aqueous stream has not been acidified, carbon bed contact is not effective for molybdenum removal.

As indicated, the carbon bed contact is effective in removing the vast preponderance of molybdenum values, eg. to 50 ppm molybdenum or less. However, in certain areas more stringent requirements call for reduction in contained molybdenum to 10 ppm or less.

Where still lower molybdenum contents are important, an especially preferred practice of the invention, after acidification and carbon bed treatment as above described, the aqueous stream passes from zone 9 via line 10 to contact zone 11 wherein the aqueous stream is contacted with a basic ion exchange resin which effectively removes additional molybdenum such that the aqueous stream exiting zone 11 via line 12 has a molybdenum content of less than 10 ppm, preferably less than 5 ppm.

Suitably, as shown, the pH of the treated aqueous stream is adjusted to 6-8 in zone 13 by addition of caustic via line 14 prior to outfall discharge via line 15.

In especially preferred practice a plurality of both carbon and ion exchange resin beds are employed. The ion exchange resin beds are conveniently regenerated by aqueous caustic wash and in especially preferred practice the wash liquid containing molybdenum removed from the resin bed is sent back to zone 4 with such molybdenum eventually being removed via the activated carbon adsorption.

As illustrated, during the regeneration cycle aqueous caustic is introduced into zone 11 via line 16 and the aqueous regeneration stream containing removed molybdenum passes via line 17 from zone 11 back to zone 4.

Carbon beds which have exhausted the ability to efficiently adsorb molybdenum values are water washed and disposed of as by drying and use as landfill or fuel.

EXAMPLE

The following example illustrates the invention with reference to FIG. 1.

The aqueous blowdown process stream from a propylene oxide/styrene monomer process after organic incineration is introduced at the rate of 24,000 lbs/hr via line 2 into cooling zone 1. The blowdown stream is comprised by weight of 86% water, 0.2% sodium molybdate, 14% sodium carbonate and bicarbonate, and 0.01% organics.

In zone 1 the temperature of the aqueous stream is reduced from 90° C. to 40° C. The cooled stream passes via line 3 to acidification zone 4 wherein the pH is reduced from 9.5 to 3 by addition of 2700 lbs/hr 94% sulfuric acid.

Carbon dioxide which is generated by reaction of carbonate salts with the sulfuric acid is removed as vapor via line 6 at the rate of 1600 lbs/hr.

The acidified aqueous stream is passed via line 7 and contacted in zones 8 and 9 with beds of activated carbon. The carbon which is employed is Calgon F-400, P-200 or React AW or equivalent. Liquid hourly space velocity is 2-10 times the bed volume per hour and the treated aqueous stream removed from the carbon bed treatment via line 10 has a molybdenum content of 30 ppm or less.

The aqueous stream passes at the rate of 25140 lbs/hr via line 10 to zone 11 wherein it is contacted at 30° C. with the weakly basic solid ion exchange resin Rohm & Haas 392 S in order to reduce the molybdenum content still further. Other similar resins such as Amberlyst A-21, or NTEC Solutions Inc. advanced affinity Chromographic (AAC) resin can be used. For best results the resin should be conditioned to the sulfate form. Liquid hourly space velocity is 4 bed volumes per hour (2-12 are generally preferred) and the aqueous stream exiting zone 11 via line 12 has a molybdenum content of less than 5 ppm.

The treated aqueous stream passes via line 12 to zone 13 wherein the pH is adjusted to 6-8 by addition of aqueous caustic via line 14. The resulting aqueous stream is conveniently discharged via line 15 to plant outfall, being of a quality which satisfies the most stringent requirements.

After an ion exchange bed has been exhausted as to its ability to remove molybdenum values, the bed is regenerated by contact with aqueous caustic introduced via line 16 with the stream containing removed molybdenum passing via line 17 to zone 4.

We claim:

1. In a process for the epoxidation of propylene to propylene oxide by reaction with organic hydroperoxide using molybdenum epoxidation catalyst wherein an aqueous molybdenum and sodium containing epoxidation process stream is obtained, the improvement which comprises acidifying the process stream, contacting the acidified stream with solid activated carbon, and recovering an aqueous stream reduced in molybdenum.

2. In a process for the epoxidation of propylene to propylene oxide by reaction with organic hydroperoxide wherein an aqueous molybdenum, sodium and organics containing epoxidation process stream is obtained, the improvement which comprises incinerating the said stream, separating an aqueous stream from the incineration containing the molybdenum and sodium values, acidifying the separated aqueous stream and separating $CO_2$ formed during acidification, contacting the remaining solution with solid activated carbon and recovering an aqueous stream reduced in molybdenum.

3. The process of claim 1 wherein the aqueous process stream is acidified to a pH of below 5.

4. The process of claim 1 wherein the aqueous process stream is acidified with $H_2SO_4$.

5. The process of claim 2 wherein said separated aqueous stream is acidified with HCl.

6. The process of claim 1 wherein the recovered aqueous stream reduced in molybdenum is contacted with a basic ion exchange resin and an aqueous stream further reduced in molybdenum is recovered.

7. The process of claim 2 wherein the recovered aqueous stream reduced in molybdenum is contacted with a basic ion exchange resin and an aqueous stream further reduced in molybdenum is recovered.

* * * * *